United States Patent

Ganshorn

Patent Number: 5,680,871
Date of Patent: Oct. 28, 1997

[54] WHOLE-BODY PLETHYSMOGRAPH

[76] Inventor: Peter Ganshorn, Goldgrund 5, D-99702 Münnerstadt, Germany

[21] Appl. No.: 550,084

[22] Filed: Oct. 30, 1995

[30] Foreign Application Priority Data

Nov. 2, 1994 [DE] Germany ............ 44 39 080.7

[51] Int. Cl.$^6$ ................................. A61B 5/08
[52] U.S. Cl. ................................. 128/720
[58] Field of Search ........... 128/600.02, 716–725, 128/727, 630; 600/21, 22

[56] References Cited

U.S. PATENT DOCUMENTS

| | | | |
|---|---|---|---|
| 3,511,237 | 5/1970 | Jaeger | 128/720 |
| 3,621,833 | 11/1971 | Crane | 128/720 |
| 4,936,308 | 6/1990 | Fukukita et al. | 128/660.02 |
| 5,513,648 | 5/1996 | Jackson | 128/721 |

FOREIGN PATENT DOCUMENTS 1566160  11/1970  Germany.

*Primary Examiner*—Jennifer Bahr
*Assistant Examiner*—Samuel Gilbert
*Attorney, Agent, or Firm*—Edwin D. Schindler

[57] ABSTRACT

Whole body plethysmograph for medical lung examinations having a pressure gauge (8) that responds to the interior pressure of cubicle (1), a pneumo-tachometer (5) which is disposed in cubicle (1) and is provided with a mouthpiece (4), a signal transmitter for the temperature difference between the inspired and the expired air, an output device (28) and an evaluation unit (7) with signal inputs (10, 18, 20, 25), to which are connected signal lines (6) from pressure gauge (8), from pneumo-tachometer (5) and from the signal transmitter for the temperature difference, having a signal output (11) for the respiratory flow rate measured by pneumo-tachometer (5) and a signal output (27) for the interior pressure measured by pressure gauge (8), which is at least partially corrected for temperature-caused pressure fluctuations by evaluation unit (7), whereby the two signal outputs (11, 27) are connected to output device (28) via signal lines (6), whereby the signal transmitter for the temperature difference is an ultrasound source and an ultrasonic sensor, which is affixed to or in mouthpiece (4) of pneumo-tachometer (5).

12 Claims, 2 Drawing Sheets

WHOLE-BODY PLETHYSMOGRAPH

BACKGROUND OF THE INVENTION

1. Technical Field of the Invention

The invention concerns a whole-body plethysmograph for medical lung examinations having an air tight, lockable cubicle for the reception of a person to be examined, a pressure gauge that responds to the interior pressure of the cubicle, a pneumo-tachometer which is disposed in the cubicle and is provided with a mouthpiece, a signal transmitter for the temperature difference between the inspired and the expired air, an output device and an evaluation unit with signal inputs, to which are connected signal lines from the pressure gauge, from the pneumo-tachometer and from the signal transmitter for the temperature difference, having a signal output for the respirator flow rate which is measured by the pneumo-tachometer and a signal output for the interior pressure measured by the pressure gauge, which is at least partially corrected for temperature-caused pressure fluctuations by evaluation unit, whereby the two signal outputs are connected to output device via signal lines.

2. Description of the Prior Art

A plethysmograph serves, as is known, to determine the airway resistance, which supplies important quantities about the condition of the bronchial flow resistance and thus the degree of lung disease. Since a direct measurement of this value is impossible, it is calculated from the flow of the expired air and the alveolar pressure. The airway resistance is measured by a pneumo-tachometer. In contrast, the alveolar pressure is not determined directly, rather is derived from the pressure in the gas tight cubicle. Because of inspiration and expiration, the volume of body of the person sitting in the cubicle changes, which becomes perceptible through small pressure fluctuations in the cubicle, which are measured by a pressure gauge. The pressure differences are so small, however, that the result is very prone to errors. Considerable falsifications of the measured values are caused above all by the temperature differences that exist between the inspired and expired air, which cause a thermal change in volume. In this way the temperature in the lung is heated to about 34.5° C., which lies below the core temperature of the lung of 37° C.

DE 15 66 160 discloses a plethysmograph with which the correction values for the temperature and air humidity are preferably adjusted manually via two independent potentiometers. The result is controlled at a recording instrument and the correction values adjusted until the curve shape of the volume change for inspiration and expiration, which is plotted via the pressure, yields approximately the same line. If the lines for inspiration and expiration are not congruent, then the pressure output value is not or not yet full corrected for possible disturbing influences (e.g. changes in the temperature or the air humidity). The disadvantage of this method is that it involves time consuming adjustment and the correction values do not adjust themselves automatically to the changed conditions. This means that the correction values for the temperature and air humidity must be reset, where necessary, during the test.

SUMMARY OF THE INVENTION

By way of contrast, the invention has the object of specifying a whole-body plethysmograph which carries out automatic error rectification for the changes in volume caused by temperature increase of the respiratory air.

In accordance with this invention, this object is solved therein that the signal transmitter for the temperature difference is an ultrasound source and an ultrasonic sensor, which is affixed in or to the mouthpiece of the pneumo-tachometer.

The essential part of the invention consists therein to measure the temperature difference between the inspired and expired air. Required for this purpose is an accurate thermometer of low inertia, since the inspiration and expiration processes follow in relatively fast succession. Therefore, an ultrasonic sensor is used which can measure the density very rapidly. As density $\rho$ is temperature-dependent according to the formula $$\rho = \frac{p}{R \cdot T}$$

the ultrasonic sensor is well suited as a thermometer. Here T is the absolute temperature, R the specific gas constant and p the pressure, which is almost constant since the respiratory movements cause only very small fluctuations in pressure. Naturally, the error can be calculated from the pressure fluctuations, since the pressure in the cubicle is measured anyway. The approximation inversely proportional to T, however, is absolutely sufficient. The ultrasonic sensor is affixed to or in the mouthpiece of the pneumo-tachometer and detects ultrasound which is dissipated by an ultrasound source. The measurement result is formatted in such a way that it corresponds to the temperature difference between the inspired and expired air and is transferred via a signal line to the evaluation unit, for example a computer, which calculates, in connection with the pressure measured by the pressure gauge and the respiratory flow rate measured by the pneumo-tachometer, a correction value for the pressure, which is deducted from the measured interior pressure of the cubicle.

The influence of the changing $CO_2$ content in the cubicle is so minor that it can be ignored.

The effects caused by the change in the air humidity are likewise minor, but noticeable. The inspired air takes up moisture in the lung, which results in an expansion of the volume. The part of external disturbing influences in the total share of more or less 9% volume changes is only 3%, so that in the most simple embodiment of the invention it is not necessary to correct pressure fluctuations which originate from the change in the air humidity.

For more accurate measurements, however, the air humidity must be considered. Since the expired air always has a relative air humidity of 100%, it is only necessary to account for the air humidity value of the inspired air, that is of the ambient air in the cubicle, as a parameter for error correction. For this, a signal transmitter for the air humidity is connected to the concerned signal input of the evaluation unit, which is, for example, a computer, via a signal line. The evaluation unit considers the change in volume which arises from the air humidity and includes this value in the calculation of the corrected interior pressure. In this manner, one obtains an output signal from which both the erroneous influences caused by temperature as well as also air humidity have been calculated and eliminated. The other disturbing influences are insignificant and can be ignored.

One possibility for transferring the value for the air humidity to the evaluation unit consists therein, as in the state of the art, to correspondingly set a controller (e.g. a potentiometer). Thereby the controller is the signal transmitter for the air humidity and is connected to the evaluation unit. Such manual correction is sufficient, since the air humidity—as mentioned above—comprises only a small part of the change in volume caused by external influences.

The relative air humidity is determined at the beginning of the lung examination and the corresponding setting made on the controller. Since the air humidity in the cubicle can change considerably during the examination, errors caused by the change in air humidity must be corrected.

Error correction for the air humidity can be achieved more easily and more comfortably, therefore, if an hygrometer is used as a signal transmitter for the air humidity. The air humidity then does not have to be determined separately and adjusted manually, but is measured in the cubicle and forwarded directly from the hygrometer to the evaluation unit via a signal line.

Since an expensive program is not required to determine the corrected interior pressure, it is preferred to set up the evaluation unit using hardware modules. The corrections can be carried out by known standard modules without software programming. As signal processing is analog, the input signals as well as the output signals issued by the evaluation unit to the output device must also be analog.

A possible circuit, which carries out the error correction, consists of a subtracter, a multiplier, an integrator as well as a diode and two potentiometers. The modules are interconnected in such a way that a correction value supplied by the multiplier is deducted from the interior pressure measured in the cubicle. The difference is then the corrected interior pressure. The correction value is obtained by multiplying a value that is dependent on the temperature and the air humidity input signal with the value of the tidal volume supplied by the integrator. The integrator itself is connected to the input signal of the respiratory flow rate via a diode. The advantage of this circuit is that it is set up simply using relatively reasonably priced standard modules, owing to which the material and production costs are low.

In the framework of the concept upon which the invention is based, the type of signal transmission in the signal lines is open to choice. Since the computer functions electronically, an electrical signal transmission presents itself. Alternatively, the signals can also be transmitted optically. Although electro-optical signal converters must then be used at the interfaces.

The output device is used to make the results visible in an appropriate manner in the most simple case, this can done with a recording instrument or an oscilloscope. In a more sophisticated embodiment, the signals from the output device are formatted and displayed on a monitor either alphanumerically or graphically.

To make it easier to retrofit the ultrasonic sensor and the ultrasound source, these two parts are integrated in a common housing, so that it is only necessary to affix the housing to or in the mouthpiece of the pneumo-tachometer and lay a signal line from the housing to the evaluation unit.

BRIEF DESCRIPTION OF THE DRAWING FIGURES

Further details, features and advantages of the invention can be taken from the following descriptive part in which a representative embodiment of the invention is explained in greater detail with the aid of the drawing. It shows in diagrammatic section:

FIG. 1 a cubicle with block diagram for the signal lines

FIG. 2 circuit diagram of the computer.

DETAILED DESCRIPTION OF THE DRAWING FIGURES

Figure 1:
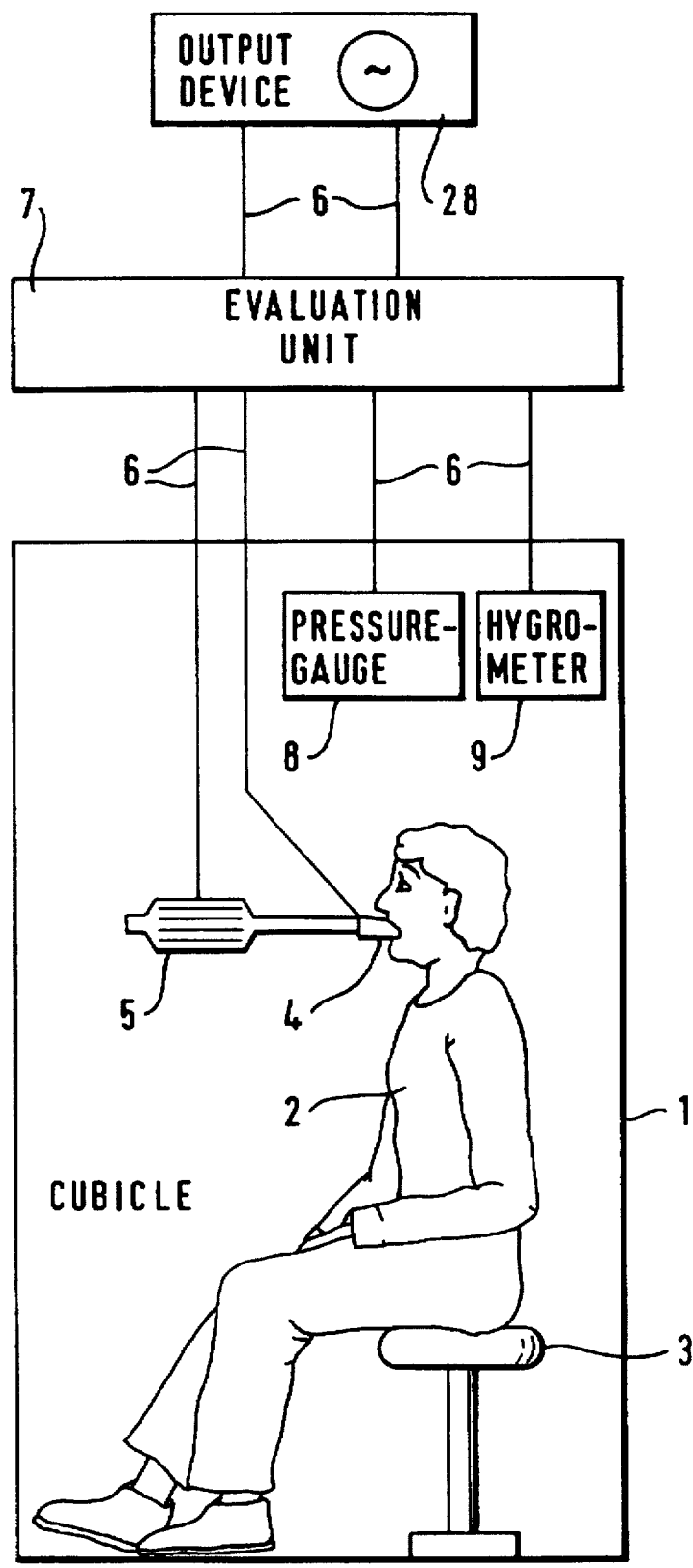
Figure 2:
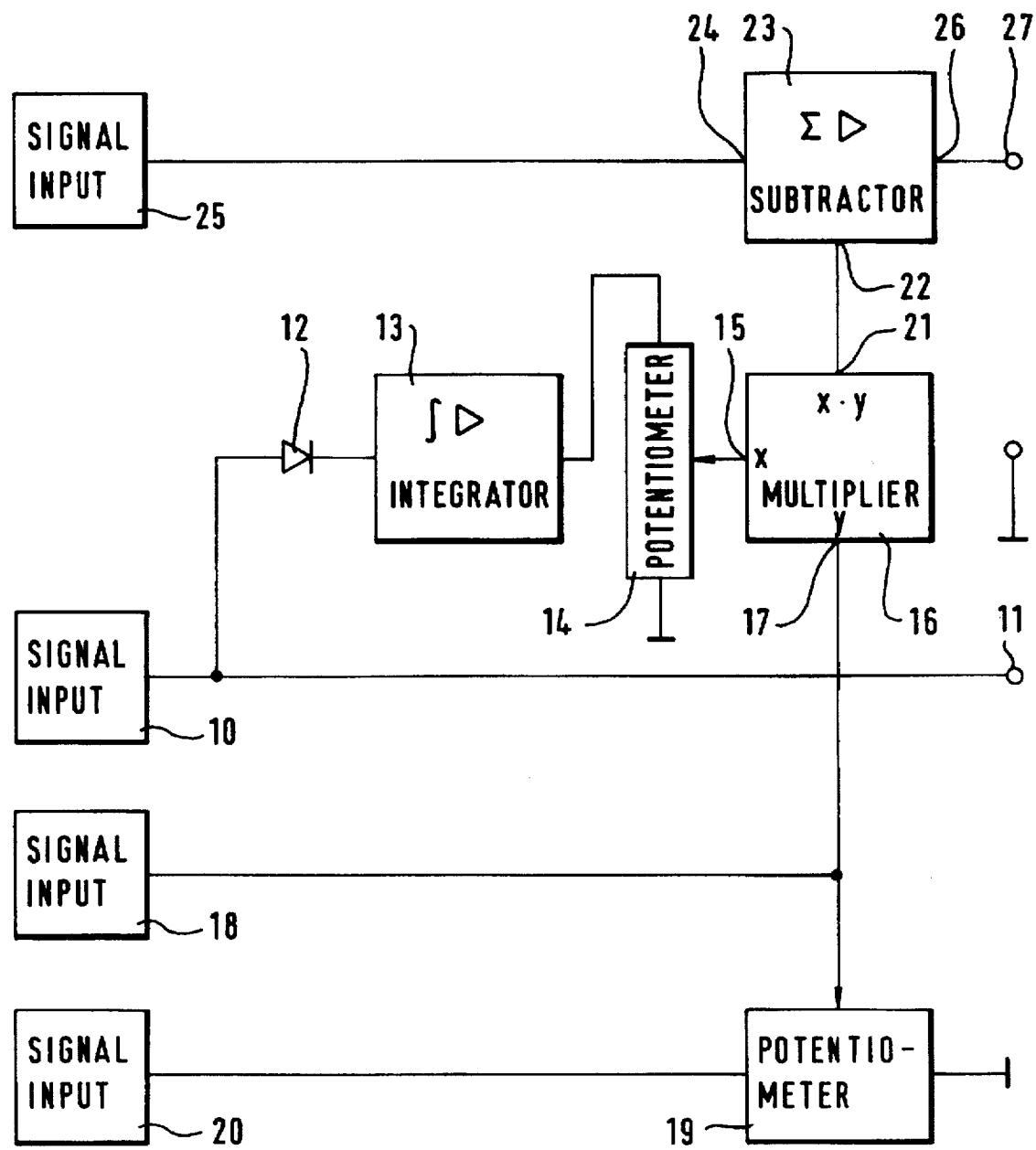

FIG. 1 shows a cubicle (1) in which a person (2) sits on a stool (3) who breathes through a mouthpiece (4) of a pneumo-tachometer (5). The respiratory flow rate measured by pneumo-tachometer (5) is muted via a signal line (6) to an evaluation unit (7), which is also connected to a pressure gauge (8) and an hygrometer (9) in the cubicle (1) likewise via signal lines (6). The output signals of evaluation unit (7) are transferred via signal lines (6) to an output device (28) (in this case an oscilloscope).

In FIG. (2) shows a circuit diagram of evaluation unit (7) with customary symbols for the modules. The signal input (10) from pneumo-tachometer (5) is directly connected to the signal output (11) for the respiratory air flew. From this connection branches a line which leads via a diode (12) to an integrator (13). The diode is polarised in such a way that it disables during an expiratory process. The output of integrator (13) is connected to the factor input (15) of a multiplier (16) via a potentiometer (14). The other factor input (17) of multiplier (16) has a direct connection to the signal input (18) for the temperature difference. To this connection is coupled a potentiometer (19) which is connected to the signal input (20) for the air humidity. The product output (21) of multiplier (16) leads to a subtrahend input (22) of subtracter (23) whose minuend input (24) is connected to the signal input (25) for the interior pressure of cubicle (1). The differential output (26) of subtracter (23) forms finally the signal output (27) for the corrected interior pressure.

I claim:

1. A whole-body plethysmograph, comprising:
   an air tight, lockable cubicle for reception of a person to be examined;
   a cubicle-pressure gauge located within said cubicle which responds to an interior pressure of said lockable cubicle;
   a pneumo-tachometer with a mouthpiece for the person to be examined, said pneumo-tachometer including an ultrasound source and an ultrasonic sensor connected to said mouthpiece for measuring a temperature difference between air inhaled and air exhaled by the person to be examined, said pneumo-tachometer being disposed within said lockable cubicle;
   an evaluation unit being connected to said cubicle-pressure gauge and said pneumo-tachometer for evaluating a corrected pressure based upon a measured pressure value taking into account a pressure fluctuation caused by the temperature difference between the air inhaled and the air exhaled by the person to be examined; and,
   an output device connected to said evaluation unit for calculating and displaying breathing resistance.

2. The whole-body plethysmograph according to claim 1, wherein said evaluation unit is a computer.

3. The whole-body plethysmograph according to claim 1, wherein said pneumo-tachometer further comprises a signal transmitter for measuring relative humidity of ambient air within said lockable cubicle for determining a relative air humidity difference between the air inhaled and the air exhaled by the person to be examined, and said evaluation unit evaluates the corrected pressure based upon a measured pressure value taking into account pressure fluctuation caused by the temperature difference and the relative air humidity difference between the air inhaled and the air exhaled by the person to be examined.

4. The whole-body plethysmograph according to claim 3, wherein said signal transmitter for the relative air humidity is an adjustable controller.

5. The whole-body plethysmograph according to claim 3, wherein said signal transmitter for the relative air humidity is a hygrometer.

6. The whole-body plethysmograph according to claim 1, wherein said lockable cubicle is connected to said evaluation unit via a first signal line and said evaluation unit is connected to said output device via a second signal line.

7. The whole-body plethysmograph according to claim 6, wherein said first signal line and said second signal line include an electrical signal transmission.

8. The whole-body plethysmograph according to claim 6, wherein said first signal line and said second signal line include an optical signal transmission.

9. The whole-body plethysmograph according to claim 1, wherein said output device is a recording instrument.

10. The whole-body plethysmograph according to claim 1, wherein said output device is an oscilloscope.

11. The whole-body plethysmograph according to claim 1, wherein said output device is a monitor with alphanumeric or graphical display.

12. The whole-body plethysmograph according to claim 1, wherein said pneumo-tachometer includes a housing and said ultrasound source and ultrasonic sensor are located in said housing.

* * * * *